(12) United States Patent
Burckhardt

(10) Patent No.: US 7,935,055 A0
(45) Date of Patent: May 3, 2011

(54) SYSTEM AND METHOD OF MEASURING DISEASE SEVERITY OF A PATIENT BEFORE, DURING AND AFTER TREATMENT

(75) Inventor: Darrell Dennis Burckhardt, Hoffman Estates, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 374 days.

(21) Appl. No.: 10/666,491

(22) Filed: Sep. 19, 2003

(65) Prior Publication Data

US 2005/0065421 A1    Mar. 24, 2005

(51) Int. Cl.
   *A61B 5/00* (2006.01)
(52) U.S. Cl. ......... 600/300; 378/21; 378/901; 382/131; 382/294
(58) Field of Classification Search ............... 600/300, 600/411, 427, 436; 378/2, 21–27, 901; 382/128–134, 276, 282, 294; 250/363.02–363.04
   See application file for complete search history.

(56) References Cited

U.S. PATENT DOCUMENTS

| | | | |
|---|---|---|---|
| 5,391,877 A * | 2/1995 | Marks ..................... | 250/363.04 |
| 5,672,877 A * | 9/1997 | Liebig et al. ............. | 250/363.04 |
| 5,803,914 A * | 9/1998 | Ryals et al. .............. | 600/407 |
| 6,065,475 A * | 5/2000 | Qian et al. ................ | 600/436 |
| 6,205,347 B1 * | 3/2001 | Morgan et al. ............ | 600/407 |
| 6,306,087 B1 * | 10/2001 | Barnhill et al. ........... | 600/300 |
| 6,339,223 B1 * | 1/2002 | Motomura et al. ....... | 250/363.07 |
| 6,490,476 B1 * | 12/2002 | Townsend et al. ........ | 600/427 |
| 6,831,961 B1 * | 12/2004 | Tybinkowski et al. .... | 378/4 |
| 6,950,542 B2 * | 9/2005 | Roesch et al. ............ | 382/128 |
| 6,965,661 B2 * | 11/2005 | Kojima et al. ............ | 378/4 |

* cited by examiner

*Primary Examiner* — A. Farah
(74) *Attorney, Agent, or Firm* — Peter L. Kendall

(57) ABSTRACT

A system for obtaining serial biochemical, anatomical or physiological in vivo measurements of disease from one or more medical images of a patient before, during and after treatment, and measuring extent and severity of the disease is provided. First anatomical and functional image data sets are acquired, and form a first co-registered composite image data set. At least a volume of interest (VOI) within the first co-registered composite image data set is identified. The first co-registered composite image data set including the VOI is qualitatively and quantitatively analyzed to determine extent and severity of the disease. Second anatomical and functional image data sets are acquired, and form a second co-registered composite image data set. A global, rigid registration is performed on the first and second anatomical image data sets, such that the first and second functional image data sets are also globally registered.

28 Claims, 5 Drawing Sheets

SYSTEM AND METHOD OF MEASURING DISEASE SEVERITY OF A PATIENT BEFORE, DURING AND AFTER TREATMENT

BACKGROUND OF THE INVENTION

1. Field of the Invention

The present invention generally relates to the diagnosis, prognosis, and severity of disease using medical images of a patient's body organs or structures of interest. In particular, the present invention relates to a system and method of measuring extent and severity of disease before, during and after treatment.

2. Description of the Background Art

Disease is any deviation from normal structure or function. A specific disease comprises symptoms manifested as specific biochemical, anatomical or physiological changes. Generally, a patient is non-invasively imaged using various imaging techniques or modalities (e.g., positron emission tomography (PET), single photon emission computed tomography (SPECT), magnetic resonance imaging (MRI), computed tomography (CT), ultrasound, fluoroscopy, x-ray, etc.) in the course of clinical examination to diagnose and determine extent and severity of disease in the patient. A measurement of disease extent is often a pre-treatment prognostic factor for overall survival. Serial post-treatment measurements of response to treatment are often stronger prognostic factors for predicting survival.

Cross or multi-modality imaging techniques (e.g., PET/CT, SPECT/CT, etc) provide physicians with composite information, which is the combination of two or more distinct registered data sets in which the properties of each data set are retained. Composite information provides physicians with the tools to localize, diagnose and stage underlying disease better than single modality information by taking advantage of attributes of both modalities. Multi-modality imaging devices are used to monitor functional and anatomical (structural) disease response (i.e., complete, partial, progressive and recurrent) to treatments. Physicians can quickly modify less effective therapy, thereby improving a patient's outcome and reducing the cost of ineffective treatment.

While functional image visualization of in vivo physiological and biochemical processes is often sufficient, volume-of-interest measurements quantitatively reflect the status of a disease. In either form (i.e., qualitative or quantitative), functional analysis often depicts the response to therapy earlier than structural changes. Generally, functional changes often precede structural changes by many days and weeks. The similarity of structural images in serial multi-modality images can serve as a basis for precise registration of serial multi-modality examinations. Registering the serial anatomical data inherently provides similar functional image registration precision.

Favorable and unfavorable prognoses are based on predictable changes of structural or functional biomarkers reflecting response of the diseased tissue to treatment. Biomarkers are detectable and measurable indicators of normal and pathological anatomic characteristics, physiologic, biochemical, or molecular parameters associated with the presence and severity of specific diseases. Physical examination, laboratory assays, and medical imaging use biomarkers to monitor health and detect disease. Since both the pathological and healing processes involve subtle increase or decrease in anatomical morphology, which occur gradually in time, a reliable measure of predictable change may be undetected, thereby reducing diagnostic accuracy. In many practical situations, the analyses of image-based functional biomarkers indicate a strong relationship of measured biomarker change to predictable specific disease even when the measurement is weak. Numerous attempts at complex computational methods that relate physiological, anatomical and molecular biological measurements to observed disease and healing processes have used logical, numerical, statistical and neural functions and systems of equations (e.g., expert systems, parametric mapping, neural networks and pharmacokinetics models) to assist in the diagnosis and prognosis of disease.

In an attempt to more accurately stage and diagnose disease, specialized nuclear medicine devices provide physicians with information about the structure and function of disease. Gamma cameras, single photon emission tomographs and positron emission tomographs are well known nuclear medicine systems that depict both tissue structure and function that is otherwise not visible by other medical imaging devices (e.g., CT, MRI, US, fluoroscopy). The application of nuclear medicine in the field of cardiology, specifically stress, rest, and redistribution myocardial perfusion SPECT imaging, exemplifies the efficiency and advantage of dedicated display and quantification of serial structural and functional images to diagnose disease and guide treatment. U.S. Pat. No. 5,803,914 to Ryals et al. discloses a method and apparatus for displaying data in a medical imaging system.

Often during diagnosis and treatment planning and monitoring, images from different modalities are inspected separately. Images from the same modality obtained at different times throughout the course of therapy are also inspected separately. Depending on the clinical requirements, a full understanding and ease of interpretation of disease requires superpositioning of anatomical and functional images of the patient. It is common practice to process patient images with the aid of a computer such that they are stereotactically reoriented and compared with normal subject images similarly processed. Automatic image alignment and volume-of-interest delineation by computer software and image visualization techniques, which are interactive and intuitive ease the visual interpretation task, are well known in the art. U.S. Pat. No. 5,568,384 to Robb et al., U.S. Pat. No. 5,672,877 to Liebig et al., U.S. Pat. No. 6,065,475 to Qian et al., and U.S. Pat. No. 6,249,594 to Hibbard disclose such systems and methods. Additionally, computer assisted methods for analyzing numerical patient data for diagnosing, screening, prognosing, and determining the severity of disease have been described, for example, in U.S. Pat. No. 6,306,087 to Barnhill et al.

Recently, multi-modality or combined devices (e.g., SPECT/CT, PET/CT, etc.) have been developed to provide both tissue anatomy and function in a single examination, with a patient in a fixed position, thereby improving the correlation of anatomical and functional images, and subsequent spatial localization of abnormalities. Such devices are disclosed in U.S. Pat. No. 5,391,877 to Marks, and U.S. Pat. No. 6,490,476 to Townsend et al. The capabilities provided by three-dimensional and even four-dimensional medical imaging modalities allow direct visualization of structure and function in vivo. However, the ability to extract objective and quantitatively accurate information from these biomedical images has not kept pace with the ability to acquire, produce, and register the images. None of the prior art references disclose the comparison of quantitative functional and structural medical image data to diagnose, prognose or determine the severity of disease using serial examinations obtained before, during, and after treatment of a patient.

Therefore, there remains a need for a system and methodology for overcoming the shortcomings of the prior art, such as a system and method of measuring extent and severity of disease before, during and after treatment of a patient.

SUMMARY OF THE INVENTION

The present invention is provided to solve the above-mentioned problems. According to an aspect of the present invention, there is provided a method of measuring extent and severity of disease in a patient. The method comprises acquiring a first anatomical image data set and a first functional image data set of the patient. The first anatomical image data set and the first functional image data set form a first co-registered composite image data set. At least a volume of interest (VOI) within the first co-registered composite image data set is identified by a user of the system. The first co-registered composite image data set including the VOI is qualitatively and quantitatively analyzed to determine extent and severity of the disease. A second anatomical image data set and a second functional image data set of the patient are acquired. The second anatomical image data set and the second functional image data set form a second co-registered composite image data set. A global, rigid registration is performed on the first anatomical image data set and the second anatomical image data set, such that the first functional image data set and the second functional image data set are also globally registered. At least a VOI within the globally registered image data set using the identified VOI within the first co-registered composite image data set is identified by the user of the system. A local, non-rigid registration is performed on the VOI within the first co-registered composite image data set and the VOI within the globally registered image data set, thereby producing a first co-registered serial image data set. The local, non-rigid registration is more precise than the global, rigid registration. The first co-registered serial image data set including the VOIs is qualitatively and quantitatively analyzed to determine severity of the disease and/or response to treatment of the patient.

According to another aspect of the present invention, there is provided a system for measuring extent and severity of disease in a patient. The system includes imaging device for acquiring a plurality of anatomical image data sets and a plurality of functional image data sets of the patient. The plurality of anatomical image data sets and the plurality of functional image data sets form a plurality of co-registered composite image data sets. Also provided is a user device for identifying at least a volume of interest (VOI) within a co-registered composite image data set of the plurality of co-registered composite image data sets, and identifying at least a VOI within a globally registered image data set of a plurality of globally registered image data sets using the identified VOI within the co-registered composite image data set. A computer system is provided, and qualitatively and quantitatively analyzes a first co-registered composite image data set of the plurality of co-registered composite image data sets including the identified VOI to determine extent and severity of the disease. The computer system further performs a global, rigid registration of a first anatomical image data set and a second anatomical image data set of the plurality of anatomical image data sets, such that a first functional image data set and a second functional image data set of the plurality of functional image data sets are also globally registered. The computer system further performs a local, non-rigid registration of the VOI within the first co-registered composite image data set and the VOI within the globally registered image data set, thereby producing a first co-registered serial image data set. The local, non-rigid registration is more precise than the global, rigid registration. The computer system further qualitatively and quantitatively analyzes the first co-registered serial image data set including the VOIs to determine severity of the disease and/or response to treatment of the patient.

BRIEF DESCRIPTION OF THE DRAWINGS

The accompanying drawings, which are incorporated herein and form part of the specification, illustrate various embodiments of the present invention and, together with the description, further serve to explain the principles of the invention and to enable a person skilled in the pertinent art to make and use the invention. In the drawings, like reference numbers indicate identical or functionally similar elements. A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

In the following detailed description of the preferred embodiment, reference is made to the accompanying drawings which form a part hereof and in which is shown by way of illustrating a specific embodiment in which the invention may be practiced. This embodiment is described in sufficient detail to enable those skilled in the art to practice the invention, and it is to be understood that other embodiments may be utilized and that structural or logical changes may be made without departing from the scope of the present invention. The following detailed description is, therefore, not to be taken in a limiting sense, and the scope of the present invention is defined by the appended claims.

Figure 1:
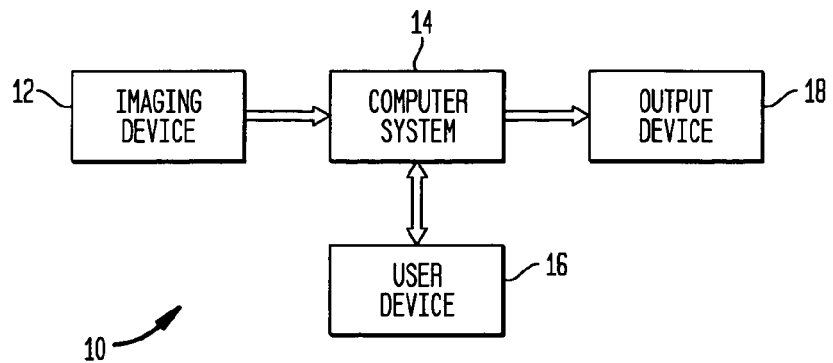
FIG. 1 schematically shows a system for measuring extent and severity of disease in a patient according to an exemplary embodiment of the present invention.

FIG. 1 schematically shows a system for measuring extent and severity of disease in a patient according to an exemplary embodiment of the present invention. Referring to FIG. 1, a system 10 comprises an imaging device 12 for acquiring anatomical and functional image data sets, a computer system 14 for processing the image data sets, and a user device 16 for displaying and manipulating the image data sets and/or images. The system 10 may also include an output device 18 for printing the image data sets or reports.

Figure 2:
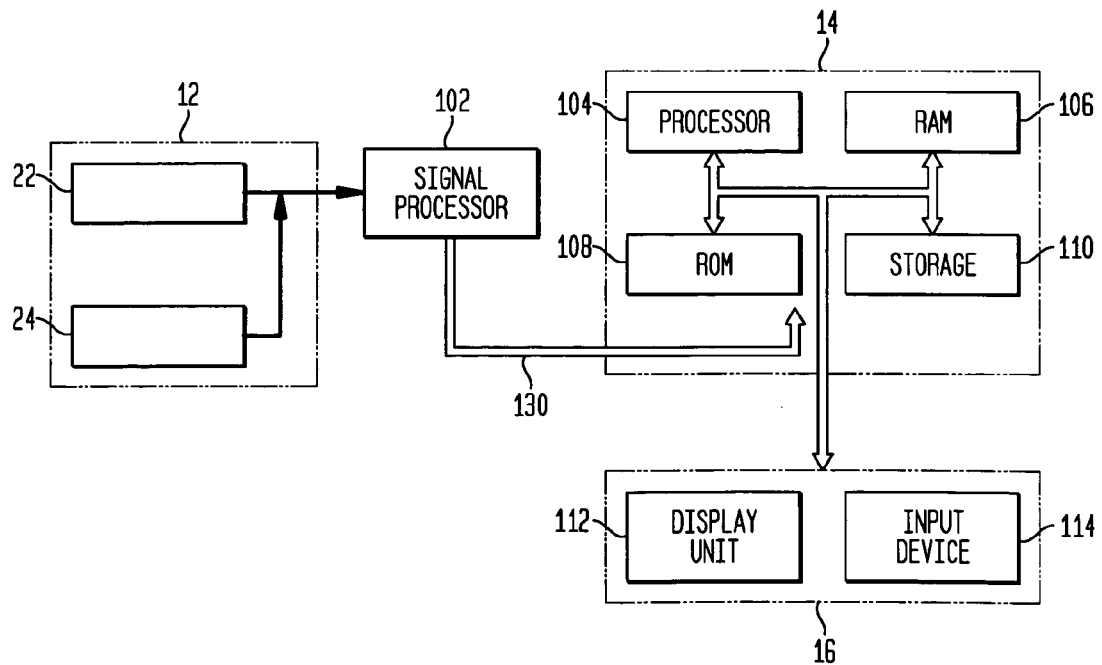
FIG. 2 is a detailed block diagram of the system for measuring extent and severity of disease in a patient as illustrated in FIG. 1.

Referring to FIG. 2, in the exemplary embodiment of the present invention, the imaging device 12 includes a computed tomography (CT) scanner 22 for acquiring a plurality of anatomical (structural) images or image data sets of a patient, and a positron emission tomography (PET) scanner 24 for acquiring a plurality of functional images or image data sets of a patient. It will be appreciated by those skilled in the art that any scanner or imaging device, such as an ultrasound imaging scanner, fluoroscopy scanner, x-ray, magnetic resonance imaging (MRI) scanner or the like, that produces anatomical image data sets, and any scanner or imaging device, such as a gamma camera, single photon emission computer tomography (SPECT) scanner, fluorescent detection scanner, optical scanner, or the like, that produces functional image data sets may be implemented in the present invention. For example, a combined CT/SPECT imaging device or separate CT and SPECT imaging devices can be implemented in the present invention. Alternatively, a single scanner that provides both anatomical and functional image data sets can be implemented in the present invention. For example, a MRI scanner can yield both anatomical and functional image data sets depending upon its use.

Anatomical data reflects the structure of the body, whereas functional data reflects the physiological process within the body. The physiological processes are often not related to structural aspects of the body, and thus, they cannot be used to derive anatomical information. For example, a CT scan may give information regarding the placement of bone and cartilage, whereas a PET scanner may be able to show physiological cellular activity indicating cancer across both bone and cartilage. The anatomical and functional image data sets are used in the present invention to locate a disease (e.g., a cancerous tumor), make an accurate diagnosis, administer proper treatment, etc. The image data sets are acquired before, during and after treatment of a patient.

The CT scanner 22 may be housed in a single CT gantry, and the PET scanner 24 may be housed in a single PET gantry. Alternatively, the CT scanner 22 and the PET scanner 24 may be housed in a combined CT and PET gantry. The scanners 22, 24 of the imaging device 12 rotate at approximately 25–35 rpm. Each gantry has dimensions of approximately 165–170 cm high and approximately 165–170 cm wide. A single patient bed (not shown) is movable between the CT gantry and the PET gantry (or combined gantry) so that a patient is placed into position for a CT scan and a PET scan during the same setting or examination. The patient bed or port defines a diameter of approximately 55–60 cm and a tunnel length of approximately 105–115 cm.

The computer system 14 includes a data bus 120 for communicating information within the system 10, a processor 104 coupled to the bus 120 for executing instructions and processing information, a random access memory (RAM) 106 coupled to the bus 120 for storing information and instructions for the processor 104, a read only memory (ROM) 108 coupled to the bus 120 for storing static information and instructions for the processor 104, and a storage medium 110 coupled to the bus 120 for storing images or image data sets.

In the exemplary embodiment of the present invention, the computer system 14 is not part of the imaging device 12, but is separate and distinct from the imaging device 12. In an alternative embodiment, the computer system 14 may be, but is not required to be, part of the imaging device 12 used to acquire the image data sets.

The computer system 14 interfaces with the scanners 22, 24 of the imaging device 12 over bus 130 via a signal processor 102. The signal processor 102 converts channel signals from the scanners 22, 24 to digital data for transmission to the computer system 14.

Figure 3C:
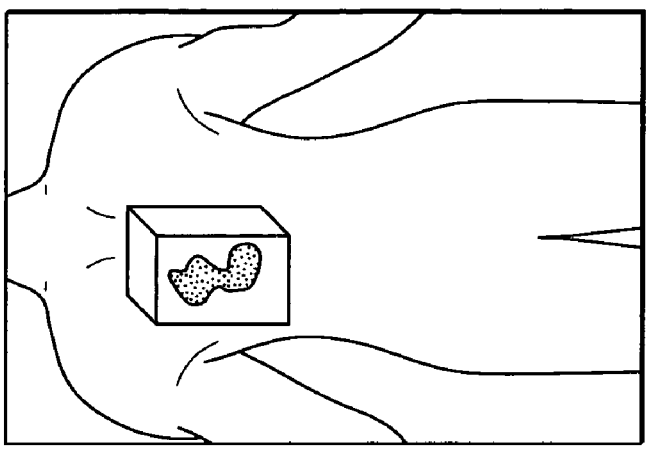
FIG. 3C illustrates a co-registered composite image data set when the anatomical image data set of FIG. 3A is registered with the functional image data set of FIG. 3B according to the present invention.
Figure 3B:
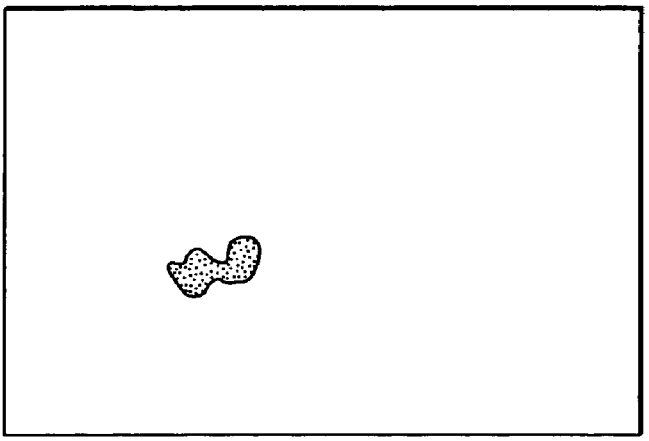
FIG. 3B illustrates a functional image data set obtained by an imaging device of the system for measuring extent and severity of disease in a patient according to the present invention.
Figure 3A:
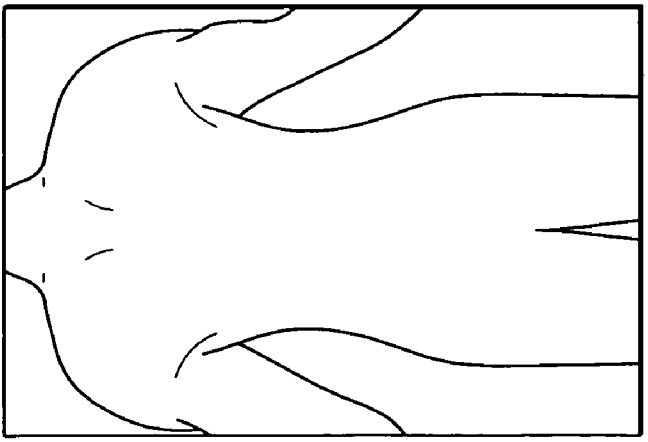
FIG. 3A illustrates an anatomical image data set obtained by an imaging device of the system for measuring extent and severity of disease in a patient according to the present invention.

The computer system 14 registers an anatomical image data set, as illustrated in FIG. 3A, with a functional image data set, as illustrated in FIG. 3B, obtained by the CT scanner 22 and the PET scanner 24, respectively. Alternatively, the image data sets may be registered directly via the imaging device 12, or via the image device 12 and the computer system 14. The registered anatomical and functional image data sets form a co-registered composite image data set, as illustrated in FIG. 3C. The anatomical, functional and composite image data sets may be saved in the storage medium 110 and/or displayed on a display unit 112 of the user device 16. The co-registered composite image data set forms a more informative image for diagnostic purposes than the images (e.g., anatomical and functional) viewed individually and unregistered.

The computer system 14 also performs a global, rigid registration of anatomical image data sets acquired at multiple stages (e.g., before, during and after treatment). For example, the anatomical image data set acquired at one stage (e.g., before treatment) is registered with the anatomical image data set acquired at another stage (e.g., after and during treatment). Accordingly, a functional image data set acquired at the same stage as its respective anatomical image data set is automatically registered with another functional image data set acquired at another stage as its respective anatomical image data set. The reason for this is that the anatomical image data sets serve as a basis for precise registration of serial image data sets since functional changes often occur quicker than anatomical changes. Thus, serial anatomical image data sets are directly registered (i.e., global, rigid registration), and thus, the functional image data sets are indirectly registered. Alternatively, the functional image data sets may be directly registered. Functional analysis often depicts a response to treatment earlier than structural/anatomical changes. A suitable global, rigid registration process may include completing a rigid matching of the anatomy to ensure global alignment. It will be appreciated by those skilled in the art that any global, rigid registration may be implemented in the present invention.

A volume of interest (VOI) is a specified multi-dimensional subset of image data voxels. Most often, a user delineates a closed path encompassing contiguous voxels to define a volume of interest (VOI) for further processing (e.g., segmenting or separating a structure from background voxels within an VOI) in order to derive volumetric attributes. Additionally, automated region segmentation methods, such as threshold and windowing, multi-spectral analysis, edge detection, region growing, active contour, and neural network models etc., are employed in the present invention to define VOIs and derive clustered voxel measurements (e.g., distance, size, position, orientation and interior, perimeter and exterior statistics). The measurements and attributes obtained from using these various techniques relay information about the tissue composition, cellular and molecular function, and the morphology of three-dimensional structures used to quantify and characterize treatment effects, extent and severity of disease.

A VOI may be selected by drawing a closed loop on a displayed image data. As such displayed image data is inherently two dimensional, a closed loop will define a two dimensional region of interest (ROI). The full VOI interest can then be derived from ROI by a number means, as discussed above. For example, the closed loop could be rotated by to define a volume. Alternatively, closed loops in the axial, coronal, and sagittal views could be used to define an asymmetrical VOI. Obviously, when a VOI is displayed on a monitor, it is seen as a two dimensional slice of the VOI, or an ROI. This can lead to confusion, as an ROI has been used in the imaging art to refer to only two dimensional regions, and to both two and three dimensional regions. In the present application, the use of the term VOI is used.

Figure 4C:
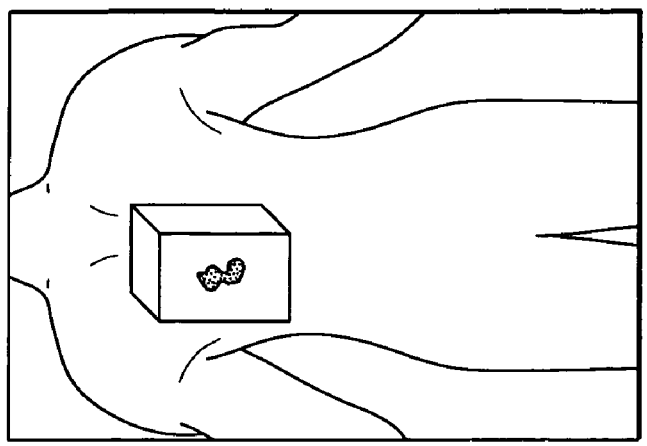
FIG. 4C shows a co-registered serial image data set produced when the VOI of FIG. 4A is registered with the VOI of FIG. 4B according to the present invention.
Figure 4B:
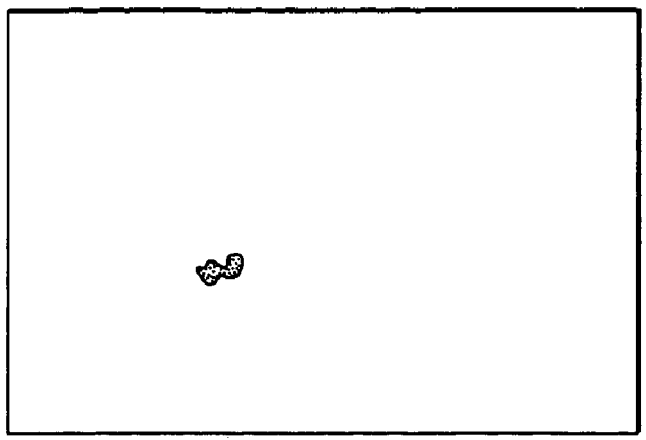
FIG. 4B shows a VOI identified in a registered image data set (e.g., a first anatomical image data set registered with a second anatomical image data set) according to the present invention.
Figure 4A:
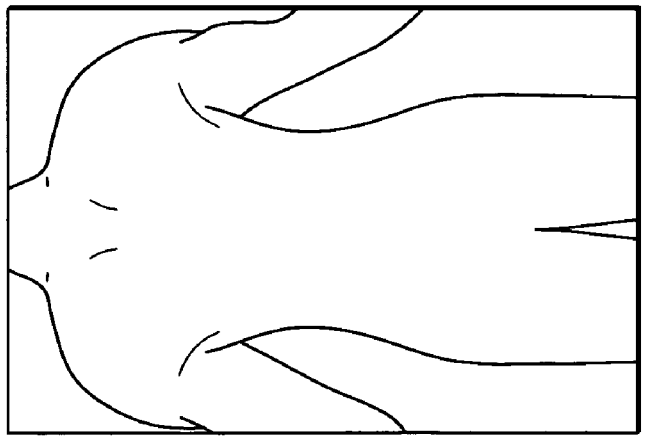
FIG. 4A shows a VOI identified in the co-registered composite image data set in FIG. 3C according to the present invention.

A VOI, as identified by the user (e.g., doctor, physician, etc.) of the system, within the co-registered composite image data set (FIG. 4A) is registered with a VOI within the registered image data set (i.e., derived from the global, rigid registration) (FIG. 4B) via the computer system 14. The regions of interest may depict organs, tumors, lesions or other objects (e.g., bone, prostheses, etc.). A deformable, local, non-rigid registration, which is more precise than the global, rigid registration, is performed on the VOI within the composite image data set and the VOI within the registered image data set, thereby producing a co-registered serial image data set (FIG. 4C). The local, non-rigid registration process may include matching of the surrounding tissue anatomy and/or function. It will be appreciated by those skilled in the art that any local, non-rigid registration may be implemented in the present invention. Further, additional local, non-rigid registration processes having varying degrees there between are performed on the image data sets.

The user device 16 interfaces with the computer system 14, and comprises a display unit 112 and an input device 114. The display unit 112 may be a cathode ray tube, liquid crystal display, plasma display, or any other suitable device that displays images or image data sets in a gray level, monotone, colored, etc. format. The input device 114 may be a keyboard, mouse, trackball, finger pad, joystick, or any other suitable device that allows a user to manipulate, select and/or define information (e.g., a volume of interest (VOI)) within the images or image data sets.

In the exemplary embodiment of the present invention, the user device 16 is not part of the computer system 14, but is separate and distinct from the computer system 14. In an alternative embodiment, the user device 16 may be, but is not required to be, part of the computer system 14.

The output device 18 may be a printer that prints reports, images, and the image data sets in black and white, gray scale, monotone, color, etc.

Figure 5A:
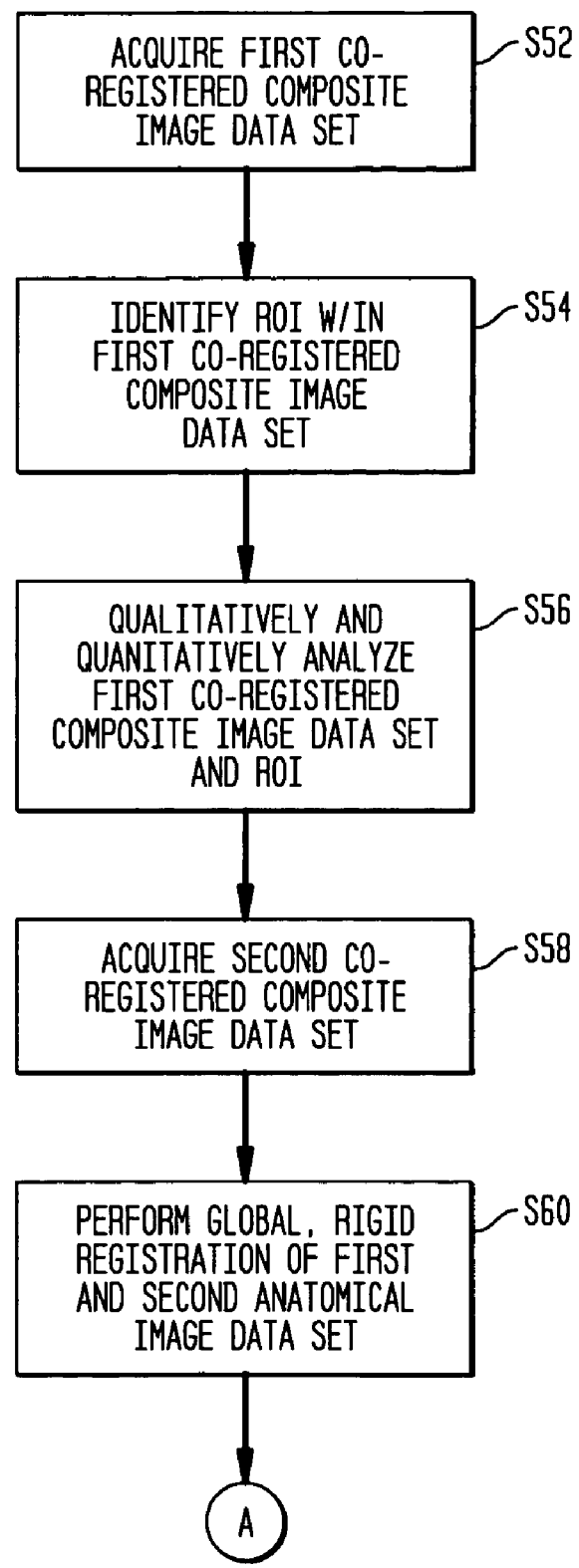
FIGS. 5A and 5B is a flow diagram of the method of measuring extent and severity of disease in a patient according to an exemplary embodiment of the present invention.
Figure 5B:
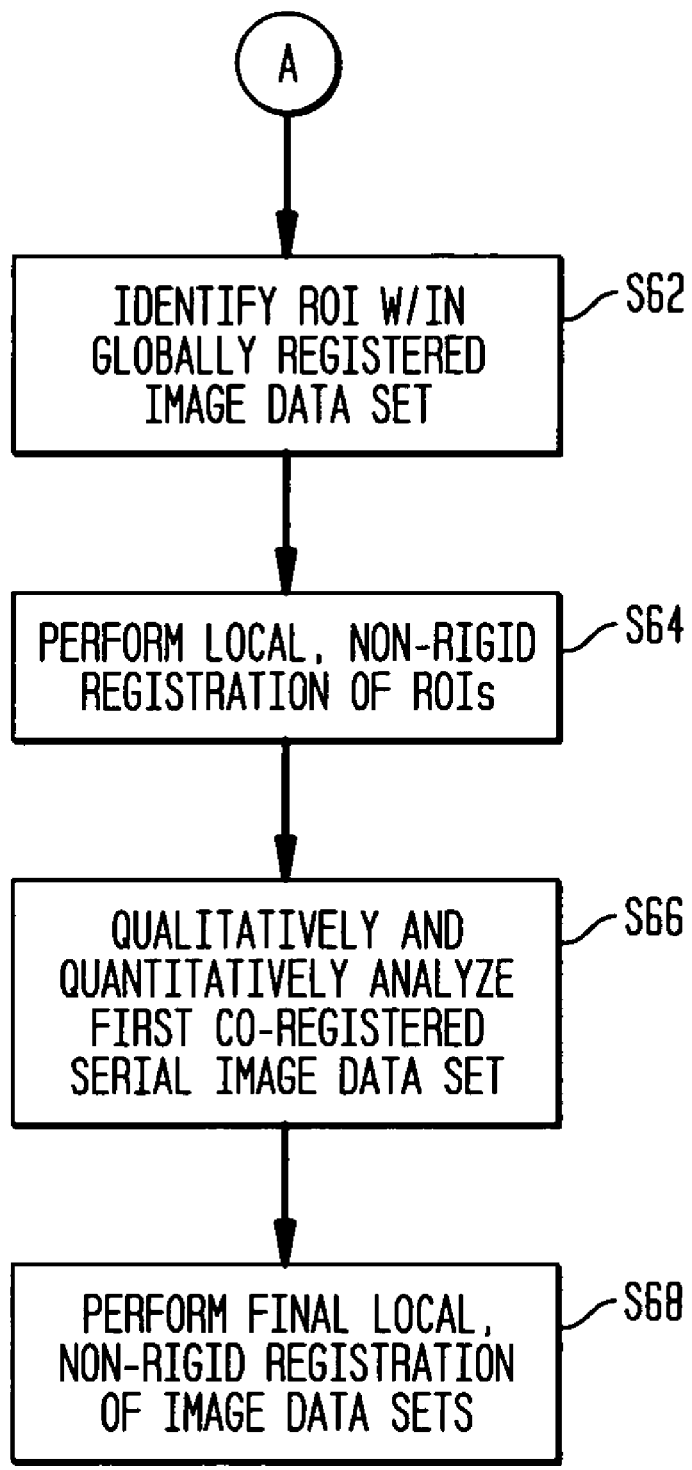

According to the method of the present invention, as illustrated in FIGS. 5A and 5B, a first co-registered composite image data set (FIG. 3C) formed of a first anatomical image data set (FIG. 3A) and a first functional image data set (FIG. 3B) is acquired via a CT scanner 22 and a PET scanner 24 of the imaging device 12, respectively, in step S52. The first image data sets are obtained before treatment of a patient, and during the same setting or examination. The first image data sets may be stored in the storage medium 110 of the computer system 14, and/or displayed on the display unit 112 of the user device 16. A user then identifies and defines a VOI within the first co-registered composite image data set (FIG. 4A) using an input device 114 of the user device 16 in step S54. The VOI may be selected from a subset of the anatomical image data set, a subset of the functional image data set, or a subset of the combined anatomical and functional image data sets (e.g., composite image data set). Quantitative information may be extracted from the VOI. The first co-registered composite image data set including the VOI are displayed on the display unit 112 of the user device 16, and qualitatively and quantitatively analyzed for extent and severity of disease in step S56. Depending on the extent and severity of the disease, the patient is therapeutically or surgically treated with the goal of eradicating the diseased tissue while minimizing damage or trauma to surrounding tissue.

During or following therapy or surgery, a second co-registered composite image data set formed of a second anatomical image data set and a second functional image data set is acquired via the CT scanner 22 and the PET scanner 24 of the imaging device 12, respectively, in step S58. The second image data sets are obtained during and/or after treatment of the patient, and during the same setting or examination. The serial image data sets provide information relating to the effectiveness of the treatment, or the progression or recurrence of the disease. The second image data sets may be stored in the storage medium 110 of the computer system 14, and/or displayed on the display unit 112 of the user device 16.

A global, rigid registration is performed on the first anatomical image data set and the second anatomical image data set, such that the first functional image data set and the second functional image data set are also globally registered in step S60. Similarly, the user defines a VOI within the globally registered image data set (FIG. 4B) using the input device 114 of the user device 16 in step S62. The VOI within the globally registered image data set is identified and defined based on the VOI within the first co-registered composite image data set. The regions of interest often reside in different locations in the serial image data sets due to changes in the patient's position, body habitus, etc. The VOI may be selected from a subset of the anatomical image data set, a subset of the functional image data set, or a subset of the combined anatomical and functional image data sets (e.g., composite image data set). Accordingly, VOI measurements from subsequent image data sets are compared against those obtained prior and throughout the course of treatment and vice versa.

The VOI defines a subset of the anatomical, functional, or composite data sets. Efficient representation of these data is necessary when defining a VOI. The nature of 2D and 3D visualization techniques that include multi-planar reformatting, volume and surface rendering techniques (e.g., is shaded and colored surfaces, transparent and semi-transparent volumes, maximum intensity projection (MIP), etc.), alpha blending, or any combination of these visualization and volume cuts is to efficiently represent these data. For example, a functional data set rendered using the MIP technique is animated to visualize structure depth. At any given projection view, a region of pixels can be selected. The actual depths of the projected voxels are unknown. Searching the volume along lines perpendicular to the voxels' projection to the displayed intensity values yields their locations. Interrogating voxels surrounding these locations for similarity to the target voxels and subsequently segmenting them from the surrounding background voxels form the VOI.

In step S64, a local, non-rigid registration is performed on the VOI within the first co-registered composite image data set and the VOI within the globally registered image data set, such that a first co-registered serial image data set is produced, as illustrated in FIG. 4C. The first co-registered serial image data set including the VOI is displayed on the display unit 112 of the user device 16, and qualitatively and quantitatively analyzed to determine severity of disease and/or response to treatment of the patient based on various measurements of both anatomy and function in step S66. Complex computations are performed to accurately measure size, shape, position, motion, intensity, and functional activity of the local image data sets. In addition to image slices corresponding to VOI data, the analyses information includes, but not limited to, tumor or lesion location in the reference image data set (e.g., slice location, bed position, etc.) or in respect to anatomic landmarks; the anatomic and functional dimensions of the tumor (e.g., length, perimeter, volume, surface area, texture, etc.); the total, mean, median, maximum, and standard deviation of pixel values representing intensity, density, activity, biological and physiological parameters (e.g., flow, metabolism, occupancy, uptake, coherence, etc.).

Local, non-rigid registrations having varying degrees therebetween may be performed on the image data sets. Thereafter, a final local, non-rigid registration is performed on the image data sets in step S68.

Anatomical landmarks or functional features in regions (VOIs) where large deformation occurred due to treatment effects cause difficulty for both local and global non-rigid registration algorithms. Additional constraints provided by the incorporation of expected deformation information obtained from previously registered VOI pairs containing substantial differences improve global non-rigid registration algorithm accuracy.

Information may be derived from the locally registered image data sets and printed in a report via output device 18, or exported for further user and computer analysis (e.g., elicit a diagnosis or prognosis or determine severity and extent of disease).

According to the present invention, a user (e.g., physician, doctor, etc.) is presented with functional and anatomical images, and quantitative measurements relating to selected structural and functional regions of interest. The information can be visualized, extracted and quantified. Further, three-dimensional, non-rigid anatomy and function information, which experience positional changes in serial medical images, can be locally and elastically matched. From the locally matched regions of interest, automated extraction and quantitation of information is obtained. The quantitative and qualitative information can be exported and summarized. The information can be transmitted for human interpretation or computer-based analysis to produce a diagnosis or prognosis of the disease, evaluate the treatment efficacy, or determine internal radiation dosimetry.

The foregoing has described the principles, embodiments, and modes of operation of the present invention. However, the invention should not be construed as being limited to the particular embodiments described above, as they should be regarded as being illustrative and not as restrictive. It should be appreciated that variations may be made in those embodiments by those skilled in the art without departing from the scope of the present invention.

While exemplary embodiments of the present invention have been described above, it should be understood that they have been presented by way of example only, and not limitation. Thus, the breadth and scope of the present invention should not be limited by the above described exemplary embodiment.

Obviously, numerous modifications and variations of the present invention are possible in light of the above teachings. It is therefore to be understood that the invention may be practiced otherwise than as specifically described herein.

What is claimed is:

1. A system for measuring extent and severity of disease in a patient, comprising:
   an imaging device for acquiring a plurality of anatomical image data sets and a plurality of functional image data sets of the patient, said plurality of anatomical image data sets and said plurality of functional image data sets form a plurality of co-registered composite image data sets;
   a user device for identifying at least a volume of interest (VOI) within a co-registered composite image data set of said plurality of co-registered composite image data sets, and identifying at least a VOI within a globally registered image data set of a plurality of globally registered image data sets using the identified VOI within said co-registered composite image data set; and
   a computer system for performing the following steps:
   qualitatively and quantitatively analyzing a first co-registered composite image data set of said plurality of co-registered composite image data sets including the identified VOI to determine extent and severity of the disease;
   performing a global, rigid registration of a first anatomical image data set and a second anatomical image data set of said plurality of anatomical image data sets, such that a first functional image data set and a second functional image data set of said plurality of functional image data sets are also globally registered;
   performing a local, non-rigid registration of the VOI within said first co-registered composite image data set and the VOI within the globally registered image data set, thereby producing a first co-registered serial image data set, said local, non-rigid registration being more precise than said global, rigid registration; and
   qualitatively and quantitatively analyzing said first co-registered serial image data set including the VOIs to determine severity of the disease and/or response to treatment of the patient.

2. The system of claim 1, wherein said imaging device includes a computed tomography (CT) scanner and a single photon emission computed tomography (SPECT) scanner.

3. The system of claim 2, wherein said CT scanner is housed in a single CT gantry, and said SPECT scanner is housed in a single SPECT gantry.

4. The system of claim 3, wherein a single patient bed is movable between said CT gantry and said SPECT gantry.

5. The system of claim 3, wherein said CT scanner and said SPECT scanner is housed in a combined CT and SPECT gantry.

6. The system of claim 5, wherein a single patient bed is movable between said CT and SPECT gantry.

7. The system of claim 1, wherein said first anatomical image data set and said first functional image data set are acquired before treatment of the patient, and said second anatomical image data set and said second functional image data set are acquired during treatment of the patient.

8. The system of claim 1, wherein said first anatomical image data set and said first functional image data set are acquired before treatment of the patient, and said second anatomical image data set and said second functional image data set are acquired after treatment of the patient.

9. The system of claim 1, wherein said first anatomical image data set and said first functional image data set are acquired during treatment of the patient, and said second anatomical image data set and said second functional image data set are acquired after treatment of the patient.

10. The system of claim 1, wherein said global, rigid registration includes rigid matching of the anatomy of the patient.

11. The system of claim 1, wherein said local, non-rigid registration includes local matching of surrounding tissues, anatomy and/or function of the patient.

12. The system of claim 1, wherein said imaging device includes a computed tomography (CT) scanner and a positron emission tomography (PET) scanner.

13. The system of claim 12, wherein said CT scanner is housed in a single CT gantry, and said PET scanner is housed in a single PET gantry.

14. The system of claim 13, wherein a single patient bed is movable between said CT gantry and said PET gantry.

15. The system of claim 13, wherein said CT scanner and said PET scanner is housed in a combined CT and PET gantry.

16. The system of claim 15, wherein a single patient bed is movable between said CT and PET gantry.

17. The system of claim 1, wherein said imaging device includes at least one of a computed tomography (CT) scanner, ultrasound imaging scanner, fluoroscopy scanner and magnetic resonance imaging (MRI) scanner providing said anatomical image data set, and at least one of a gamma camera, positron emission tomography (PET) scanner and single photon emission computer tomography (SPECT) scanner providing said functional image data set.

18. The system of claim 1, wherein said imaging device is a single scanner capable of acquiring both said anatomical image data sets and said functional image data sets.

19. The system of claim 1, wherein said system further comprises an output device for printing reports, images, and the various image data sets.

20. The system of claim 1, wherein said user device comprises a display unit for displaying the various image data sets, and an input device for selecting said VOI within the various image data sets.

21. The system of claim 1, wherein said computer system comprises a storage means for storing the various image data sets.

22. The system of claim 1, wherein said computer system further performs the step of performing a final local, non-rigid registration of the image data sets, wherein the local registration steps have varying degrees therebetween.

23. The system of claim 1, wherein, the VOIs are selected from a subset of said anatomical image data sets.

24. The system of claim 1, wherein the VOIs are selected from a subset of said functional image data sets.

25. The system of claim 1, wherein the VOIs are selected from a subset of said anatomical image data sets and a subset of said functional image data sets.

26. The system of claim 1, wherein the qualitative analysis includes determining at least one of a presence, absence and location of the disease, and number of tumors.

27. The system of claim 1, wherein the quantitative analysis includes determining at least one of a mean, deviation, size and shape of disease in the functional image data sets.

28. The system of claim 1, wherein the quantitative analysis includes determining at least one of a texture, size and shape of disease in the anatomical image data sets.

* * * * *